(12) United States Patent
Feller

(10) Patent No.: US 7,156,856 B2
(45) Date of Patent: *Jan. 2, 2007

(54) METHOD AND APPARATUS FOR FOLLICULAR EXTRACTION AND TRANSPLANTATION

(76) Inventor: Alan S. Feller, 287 Northern Blvd., Suite 200, Great Neck, NY (US) 11021

( * ) Notice: Subject to any disclaimer, the term of this patent is extended or adjusted under 35 U.S.C. 154(b) by 542 days.

This patent is subject to a terminal disclaimer.

(21) Appl. No.: 10/425,211

(22) Filed: Apr. 29, 2003

(65) Prior Publication Data

US 2004/0220589 A1  Nov. 4, 2004

(51) Int. Cl.
*A61B 17/50* (2006.01)
(52) U.S. Cl. ........................ 606/133
(58) Field of Classification Search ........... 606/133; 60/644.1
See application file for complete search history.

(56) References Cited

U.S. PATENT DOCUMENTS

| | | | |
|---|---|---|---|
| 3,867,942 A | 2/1975 | Bellantoni et al. | |
| 4,122,855 A | 10/1978 | Tezel | |
| 4,476,864 A | 10/1984 | Tezel | |
| 4,875,288 A | 10/1989 | Trotta et al. | |
| 5,417,683 A | 5/1995 | Shiao | 606/1 |
| 5,439,475 A | 8/1995 | Bennett | |
| 5,578,054 A | 11/1996 | Arnold | |
| 5,611,811 A | 3/1997 | Goldberg | 606/187 |
| 5,693,064 A | 12/1997 | Arnold | 606/184 |
| 5,827,297 A | 10/1998 | Boudjema | 606/133 |
| 5,895,403 A | 4/1999 | Collinsworth | |
| 5,922,000 A | 7/1999 | Chodorow | |
| 5,951,572 A | 9/1999 | Markman | 606/133 |
| 5,989,273 A | 11/1999 | Arnold | 606/187 |
| 5,989,279 A | 11/1999 | Rassman | 606/187 |
| 6,027,512 A | 2/2000 | Bridges | 606/131 |
| 6,059,807 A | 5/2000 | Boudjema | 606/187 |
| 6,461,369 B1 | 10/2002 | Kim | 606/187 |

*Primary Examiner*—Michael J. Hayes
*Assistant Examiner*—M. Thomas Andersen
(74) *Attorney, Agent, or Firm*—Kenyon & Kenyon LLP

(57) ABSTRACT

Apparatus and method are for extraction of follicular units. A dermal biopsy punch is utilized in combination with a suction device for extraction purposes. The use of suction to extract the follicular unit allows for distribution of the forces over a large area of the unit, helping to keep the unit intact. A perforating device, affixed to the punch, is utilized to weaken the structural integrity of the extraction area. The perforating device, having a single spike member which is inserted into the skin at a small, previously determined depth, in several locations, surrounding the follicular unit and reducing the holding tissue around the unit. The spike member of the perforating device is relatively thin and unlikely to damage the follicular unit. Because suction is utilized to extract the follicular unit, the distal end of the apparatus may have a guard which functions to prevent the extracted follicular units from being vacuumed further therein.

11 Claims, 5 Drawing Sheets

METHOD AND APPARATUS FOR FOLLICULAR EXTRACTION AND TRANSPLANTATION

BACKGROUND OF THE INVENTION

1. Field of the Invention

The present invention is a method and apparatus for extraction of follicular units from a donor area, for the purpose of transplantation into balding areas of the scalp.

2. Description of the Prior Art

Numerous innovations for hair transplant procedures have been provided in the prior art that are described as follows. Even though these innovations may be suitable for the specific individual purposes to which they address, they differ from the present invention as hereinafter contrasted. The following is a summary of those prior art patents most relevant to the invention at hand, as well a description outlining the differences between the features of the present invention and those of the prior art.

1. U.S. Pat. No. 5,989,279, invented by Rassman, entitled "Hair Implantation Device"

The patent to Rassman describes a system for transplanting hair grafts from a donor region of a patient's scalp to a recipient region of the patient's scalp. The system includes harvesting N (N≧21) strips of skin containing living hair follicles from the donor region of the patient's scalp, the N strips of skin being harvested simultaneously, and cutting the N strips of skin into hair grafts, the N strips of skin being cut simultaneously. The system also includes loading the hair grafts sequentially, bottom down, into a removable cartridge connected to an instrument for implanting the hair grafts into the recipient region of the patient's scalp, the hair grafts being loaded so as to create an air seal between the hair grafts and the cartridge, and implanting the hair grafts. The implanting includes implanting the hair grafts into the recipient region of the patient's scalp, one at a time, using the instrument, by feeding a hair graft to a predetermined feed position in the instrument via air suction created by an air seal between the hair graft and the cartridge, making an incision at a point in the recipient region of the patient's scalp at which the hair graft is to be implanted using a cutting device on the instrument, and sliding the hair graft into the incision using an implanting member in the instrument.

Other relevant prior patents to Rassman include U.S. Pat. No. 5,782,851, entitled "Hair Transplantation System," U.S. Pat. No. 5,817,120, entitled "Hair Implanting Instrument," and U.S. Pat. No. 5,584,841, entitled "Instrument For Implanting Hair Grafts".

2. U.S. Pat. No. 5,989,273, invented by Arnold, entitled "Apparatus For Producing Hair Transplantation Donor Strips And Methods"

The Arnold invention provides methods and apparatus for producing hair transplantation donor strips for use in hair transplantation procedures. According to one exemplary method, a surgical instrument is provided having at least two planar blades, with each blade having a sharpened edge, and with the blades being substantially parallel to each other. The blades are translated along and through an area of the scalp having hair to form at least two parallel incisions in the scalp. The orientation of the blades relative to the hair is adjusted such that the blades are generally aligned at all times with the direction of hair growth for the hair between the blades when the surgeon is making the incisions. A graft of skin having hair is then removed from between the incisions formed by the blades. At least a portion of the graft of skin having at least one hair is then placed into another area of the scalp.

3. U.S. Pat. No. 6,027,512, invented by Bridges, entitled "Hair Follicle Harvesting Device"

The patent to Bridges describes a hair follicle harvesting device which is characterized by a pencil-like harvesting tube fitted at the distal end with a needle of selected bore size for insertion over one or more hairs and hair follicles in a scalp flap and puncturing the scalp flap. The harvesting tube is connected at the proximal end to a source of saline solution and accommodates a flow of saline solution through a venturi or tube constriction by operation of a pump to remove the encircled and loosened hair follicles as micrografts, minigrafts and hair plugs from the scalp flap. The hair follicles are caused to flow through the needle and into the saline solution stream by reduced pressure responsive to flow of the saline solution through the venturi or tube constriction located near the base of the needle in the harvesting tube. The saline stream containing the hair follicles is then directed from the harvesting tube through a screen in a disposable follicle harvesting apparatus or a screen in a follicle collection vessel, which retains the hair follicles on the screen and returns the saline solution to the pump for continued circulation through the harvesting tube. The screen is periodically removed from the harvesting apparatus or follicle collection vessel to collect the harvested hair follicles, which are then used in conventional hair transplant procedures.

4. U.S. Pat. No. 5,611,811, invented by Goldberg, entitled "Micro And Mini Hair Transplant Device"

The patent to Goldberg describes a device for automating hair transplant procedures. The device includes a part for puncturing the scalp, a part for containing the hair grafts to be transplanted, a part for ejecting the hair grafts from the containing means, a part for actutating the ejecting means and a part for delivering the hair grafts into the transplant site.

5. U.S. Pat. No. 5,827,297, invented by Boudjema, entitled "Device For Transplanting Small Diameter Hair Grafts"

The patent to Boudjema describes a device for transplanting small diameter hair grafts using a hand-held cutting instrument having a body holding the tool, a rotary cylindrical tool and a drive assembly capable of driving the tool in rotation with respect to the body. The tool has a hollow end for cutting a graft. The cylindrical tool is a hollow needle with an axial through bore of the same diameter as the hollow cutting end to which it forms an extension. The device extracts the graft by sucking it up through the axial bore of the needle.

6. U.S. Pat. No. 5,693,064, invented by Arnold, entitled "Dermal Punch For Hair Transplantation And Methods"

In one aspect, the Arnold invention provides a method for transplanting hair. According to the method, an instrument is provided having a concentric cylindrical shaft having a proximal end, a distal end, and an axis extending therebetween A blade is on the distal end of the shaft normal to the axis of the shaft, and an escape port is provided in the wall of the shaft near the distal end. The instrument is inserted into the skin to a preselected depth where the skin is below the escape port to form a cylindrical incision. The instrument is then removed from the skin. The step of inserting the instrument into the skin is repeated, with any accumulated skin in the shaft being forced through the escape port. In this way, the shaft does not become clogged with tissue after repeated use. A graft of skin having at least one hair is then placed into at least one of the cylindrical incisions.

7. U.S. Pat. No. 6,059,807, invented by Boudjema, entitled "Device For Implanting Small-Diameter Capillary Grafts"

The patent to Boudjema describes a device for implanting a small-diameter capillary graft into the scalp, comprising a hollow needle pierced by a throughbore having a smaller diameter than the graft and suitable for gripping, by its end, one end of the said graft through the needle. The needle is mounted so as to slide in a cylindrical sheath between a first position, in which the needle is retracted inside the sheath, and a second position for gripping and for inserting the graft into the scalp, in which the needle projects beyond the end of the sheath. The needle is actuated between the first and second positions, preferably by application and release of a vacuum to an enclosure which is defined by a cylindrical tube and which is closed on a first side by the sheath and on a second side by a plug fastened to a distal end of the needle. A communication port is formed in the needle communicating with the enclosure, so as to allow vacuum in the enclosure to facilitate gripping of the capillary graft by vacuum, and an orifice is provided in a wall of the cylindrical tube so as to allow a surgeon rapidly to apply and release vacuum in the enclosure.

8. U.S. Pat. No. 5,417,683, invented by Shiao, entitled "Mini-Graft Hair Implanting Device For Implanting Multiple Clumps Of Hair Follicles At One Time"

The patent to Shiao describes a mini-graft hair implanting device for implanting multiple clumps of hair follicles at one time includes a barrel, a plunger and a depth control unit. The barrel is formed as a hollow cylinder with an open top and a bottom wall that has a cluster of hollow needles which are attached thereto so as to extend downwardly therefrom. Each of the hollow needles is adapted to receive a clump of hair follicles therein and has two open ends, a distal one of which is tapered so as to form a pointed tip. The plunger extends slidably into the barrel and has a bottom end that is formed with a set of downwardly extending first push rods and at least one downwardly extending second push rod. The first push rods are aligned with and extend into the hollow needles. The depth control unit is attached to and extends downwardly from the bottom wall of the barrel. The depth control unit includes at least one tube which is shorter than the hollow needles and which has two open ends, a distal one of which is blunt. Each second push rod is aligned with and extends into a corresponding tube.

9. U.S. Pat. No. 6,461,369, invented by Kim, entitled "Hair Transplanter"

The Kim invention discloses a hair transplanter. A needle to be inserted into a scalp has a pointed end portion to reduce damage of the scalp, and a guide plate in adhered to an end portion of a sliding unit reciprocating in the longitudinal direction of the needle outside the needle, in order to prevent hair roots from being separated at the time of the separation of the needle. As a result, the hair roots inserted into a needle insertion groove are not damaged and are naturally settled in the scalp without modification, thereby stably performing the hair transplantation.

10. U.S. Pat. No. 5,951,572, invented by Markman, entitled "Method, Apparatus And Kit For Performing Hair Grafts"

In the patent to Markman, a device and method are set forth for performing hair grafts which includes a housing, plunger with a needle, and a carriage containing an inventory of hair grafts to be placed. The plunger is placed at an extended position where the needle extends from the catheter and the needle and catheter are inserted into the tissue. The plunger and needle are withdrawn and the carriage is indexed to position a graft. The plunger is moved to urge the graft from the carriage through the catheter into the tissue for transplantation.

The above-listed prior art largely relates to methods known in the art, such as the "strip method" (first-above-listed patent to Rassman, second above-listed patent to Arnold) as well as cylindrical cutting tools for extraction, and various hollow needles used in the extraction process. In addition, various prior art relates to the implantation of follicular units, as distinguished from device designed to facilitate extraction.

In contrast to all of the above, the present invention provides an innovation to improve follicular unit extraction.

The innovation utilizes a perforator with a thin spike inserted repeatedly into the skin around the follicular unit to weaken the structural integrity of the area. Because the follicular unit is being partially sucked into the punch, the holding tissue is decreased, allowing the follicular unit to become free. This prevents damage to the follicular units safely extracts high quantities of follicular units in a short period of time, while maintaining the integrity of such follicular units.

SUMMARY OF THE INVENTION

As noted, the present invention is an improved method and apparatus for extraction of follicular units from a donor area, for the purpose of transplantation into balding areas of the scalp.

Recent methods of extraction include the usage of a 1 mm dermal biopsy punch (placed over the follicular unit and pushed through the skin) in combination with a fine forceps (for subsequent "plucking" of the follicular unit). Such often leads to portions of the follicular unit being shaved off by the punch, injuring or killing the unit. Attempts to solve this problem include the sliding of the punch only part way down, and pulling the partially freed follicular unit with fine forceps until the remaining supporting dermis gives way. This, however, leads to crushing or tearing of the follicular unit, as well as lengthy delays between each extraction.

The present method and apparatus seek to circumvent the above-described problems. The first method utilizes the previously-existing dermal biopsy punch in combination with a suction device for extraction purposes. The suction allows for distribution of forces over a greater area of the follicular unit than previously attained. This mitigates the "crush force" upon the follicular unit, thus helping keep the unit intact. Moreover, because this method does not require repeatedly putting down the punch and picking up the forceps, the extraction process is sped up significantly.

The present invention also utilizes a perforating device that is designed to weaken the structural integrity of the area in question, which greatly facilitates extraction of the follicular unit. The perforation device comprises a "spike" member which is repeatedly inserted around the follicular unit into the skin at a small, previously-determined depth. Because this takes place while the follicular unit is being partially sucked into the punch, the holding tissue is then decreased, allowing the follicular unit to become free. Because the device utilizes suction as a means of extraction rather than collection of follicular units, the distal end of the device comprises a guard which functions to prevent the extracted follicular units from being vacuumed further therein.

Importantly, because the spike is relatively thin, the device is unlikely to damage the follicular units. In addition, because the perforator weakens the surrounding tissue, the device allows patients with strong dermal connective tissue to be candidates for the procedure. In total, the present invention provides a safe means to extract significant quantities of follicular units in a relatively short period of time, while maintaining the integrity of such follicular units.

In light of the foregoing, it is generally an object of the present invention to provide an effective means to extract follicular units from a donor area and transplant same into balding areas of the scalp It is also an object of the invention to provide an extraction means that maintains the integrity of the follicular unit.

It is a specific object of the present invention to provide an effective extraction means that does not rely upon the usage of forceps, which often crush or tear the follicular unit.

It is also an object of the invention to utilize a perforating device with a spike member, designed to weaken the structural integrity of the area in question, greatly facilitating extraction of the follicular unit.

It is another object of the present invention to provide the perforator with a spike that is unlikely to damage the follicular unit in question.

It is a further object of the invention to uniquely utilize suction as a means of extraction, as distinguished from a means of collection of follicular units.

It is a further object of the present invention to provide a device with a follicular unit guard which functions to prevent extracted follicular units from being vacuumed further within the device.

It is also an object of the present invention to allow patients with strong dermal connective tissue to be candidates for the extraction and placement procedure.

It is an additional object of the invention to provide an extraction means that is significantly faster than those of the prior art, increasing the efficiency of the procedure and decreasing the cost of the procedure for the patient.

Finally, it is also an object of the present invention to provide a safe means to extract significant quantities of follicular units in a relatively short period of time.

The novel features which are considered characteristic for the invention are set forth in the claims. The invention itself, both as to its construction and its method of operation, together with additional objects and advantages thereof, will be best understood from the following description of the embodiments when read and understood in connection with accompanying drawings.

BRIEF DESCRIPTION OF PREFERRED EMBODIMENTS

DETAILED DESCRIPTION OF THE PREFERRED EMBODIMENT

As noted herein, recent methods of extraction include the usage of a 1 mm dermal biopsy punch placed over the follicular unit and pushed through the skin. Such is in combination with a fine forceps, used for subsequent "plucking" of the follicular unit. However, this procedure often leads to portions of the follicular unit being shaved off by the punch, with the remainder of the follicular unit attached to connective tissue. Thus, the fine forceps of the known procedure result in the injuring or killing the entire follicular unit, in turn defeating the purpose of extraction for transplantation.

Attempts to solve this problem include the sliding of the punch only part way down, and pulling the partially freed follicular unit with fine forceps until the remaining supporting dermis gives way. This, however, often leads to crushing or tearing of the follicular unit, as well as lengthy delays between each extraction.

Figure 1:
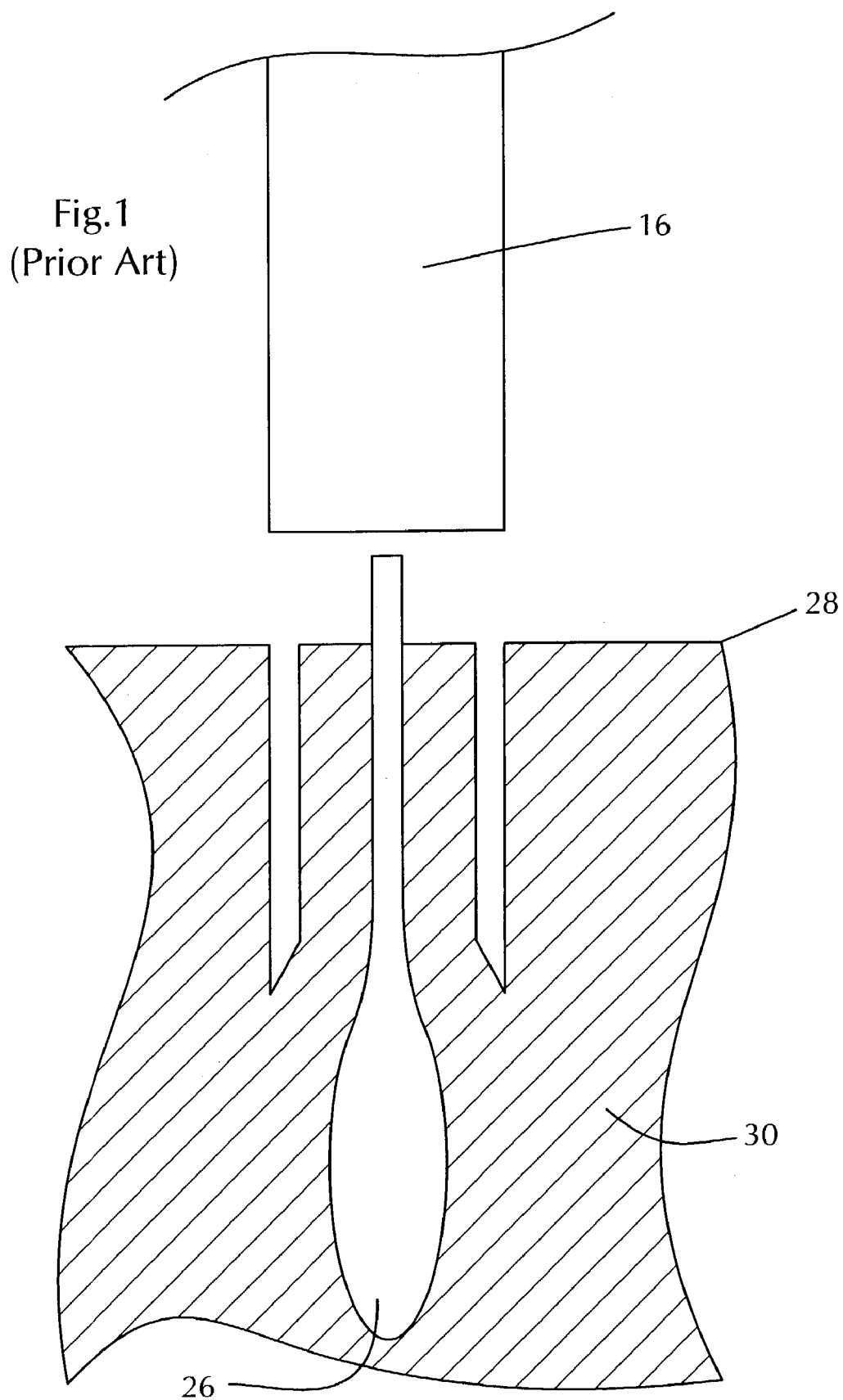
FIG. 1 depicts a prior art method and apparatus, for the purposes of discussion, illustrating a previously-existing punch approaching a follicular unit.
Figure 2:
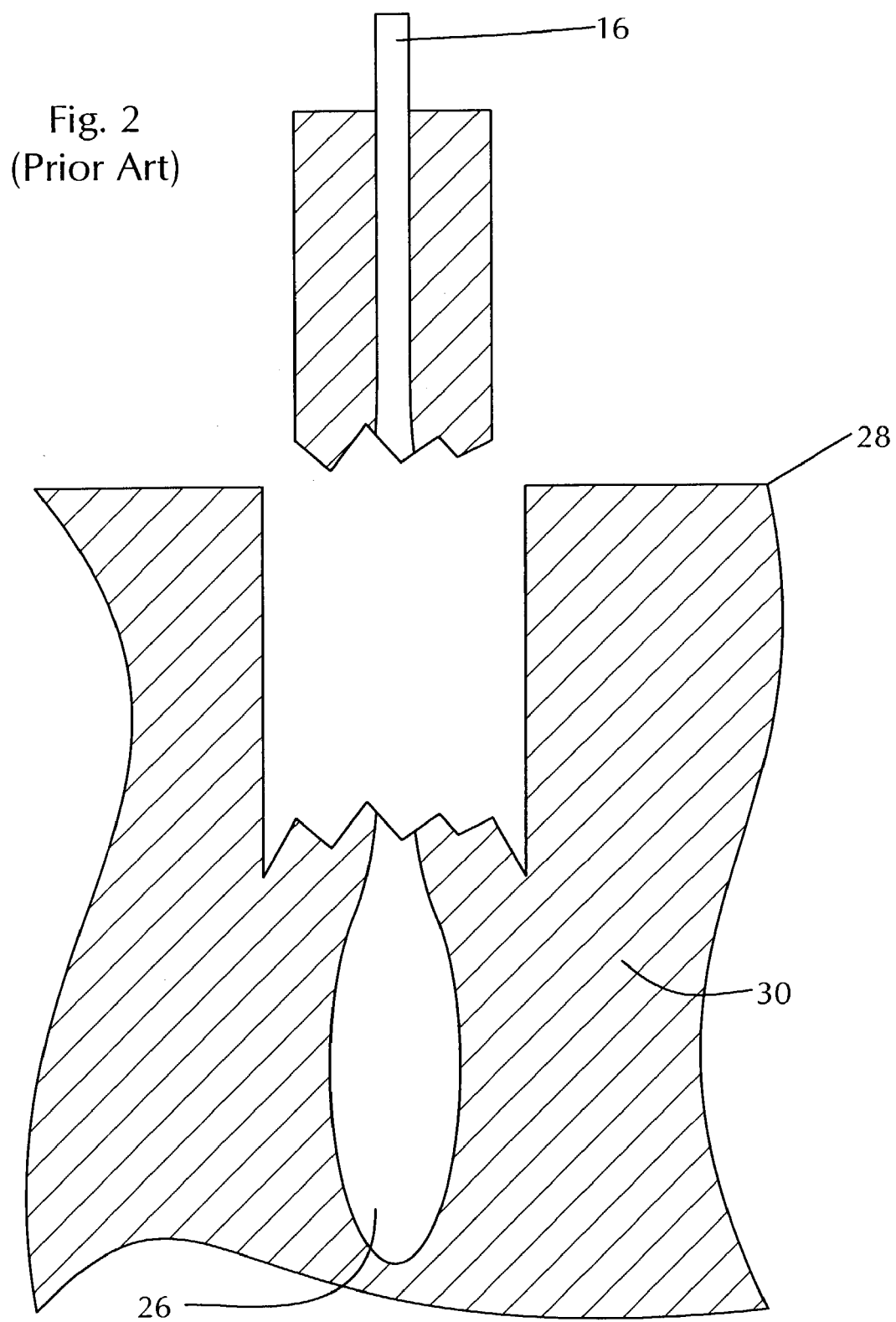
FIG. 2 depicts a prior art method and apparatus, for the purposes of discussion, illustrating a follicular unit broken off through usage of the previously-existing punch mechanism.

To illustrate the typical problem of currently used procedures, FIG. 1 is a view of prior art, shown for the purpose of discussion, showing a previously-existing punch (16) approaching a follicular unit (26), a large portion of which is below the skin like (28) and within the scalp area (30). In addition, FIG. 2 is a subsequent view of a common prior art method, illustrating the follicular unit (26) broken off through usage of the prior method.

It should also be noted that because follicular units are not always parallel to the punch along the vertical axis, additional tearing and breaking problems often occur. For the purposes of example, if the portion of the follicular unit below the skin line in FIG. 1 were to be rotated to a degree approaching perpendicular to the skin line, the biopsy punch, when be pushed downwardly, would shear the follicular unit, injuring or killing the same.

Thus, based on the foregoing, a significant need exists for an apparatus and method for follicular unit extraction that dispenses with the need for fine forceps, and which is less likely to cause follicular unit damage than the standard biopsy punch.

Figure 3:
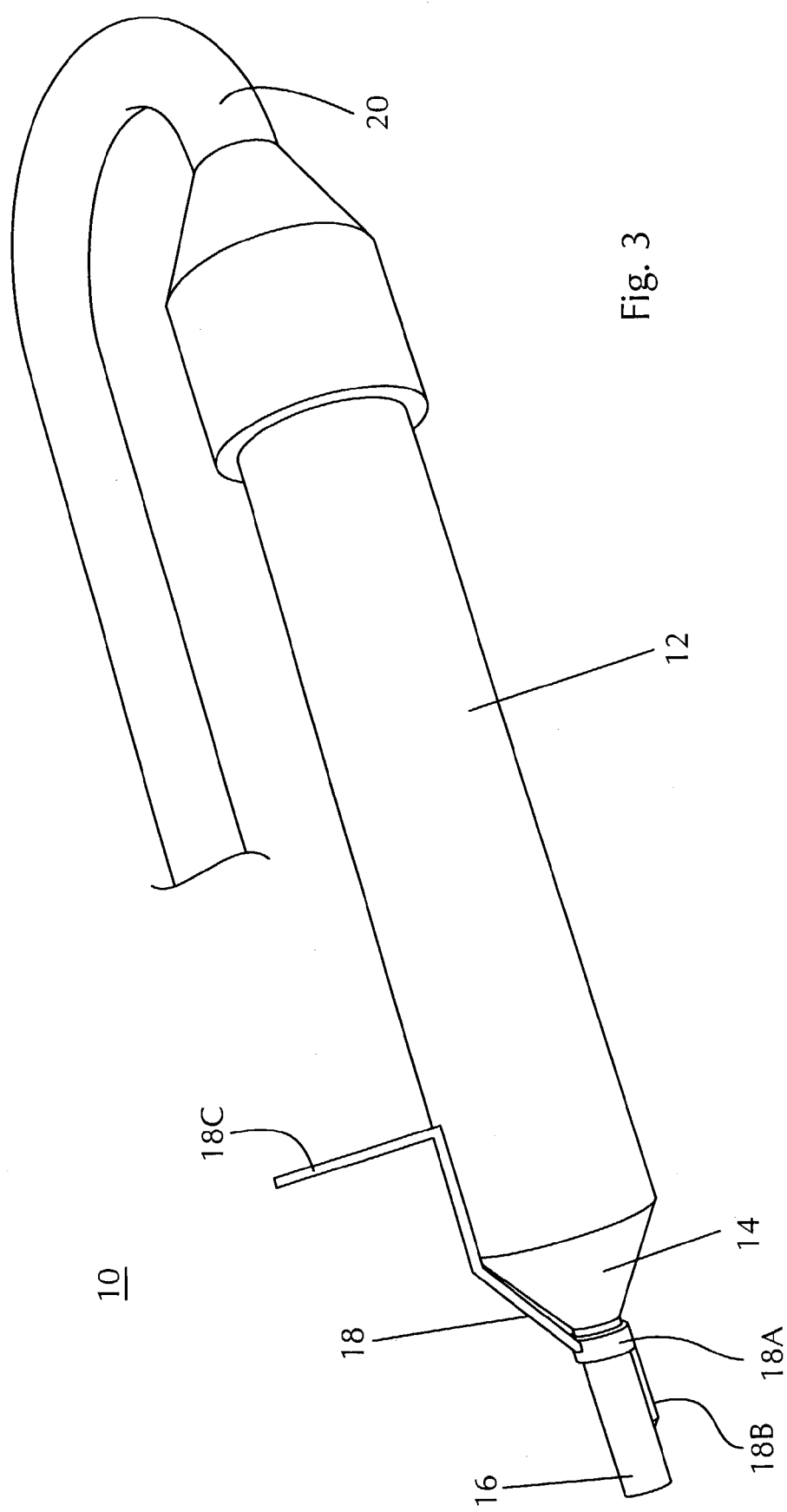
FIG. 3 is a perspective view of the present invention, including punch device, perforating mechanism thereon, handle, and components of suction means.

The present invention, through usage of items such as suction and a perforator, accomplishes the above objectives. FIG. 3 is a perspective view of a preferred mode of the present invention, including its punch device, perforating mechanism, handle, and suction means components.

Specifically, the apparatus for follicular extraction (10) comprises a generally elongated handle (12) to be engaged by the user. The handle (12) comprises a tapering portion (14) at the front or distal end. A small, generally cylindrical biopsy punch (16) is removably attached to the tapering portion of the handle (14). As noted, the punch may be a standard 1 mm biopsy punch to accomplish the purposes of the invention.

A perforator (18) is affixed to the punch (16). The perforator comprises an annular portion (18A), with an open end to allow the same to fit around the punch (16). The perforator further comprises a single spike member (18B), which extends along the vertical axis of the punch, generally parallel thereto. The perforator also comprises an extended member or handle portion (18C), which is of a shape that corresponds to and abuts the tapering portion of the handle

Figure 5:
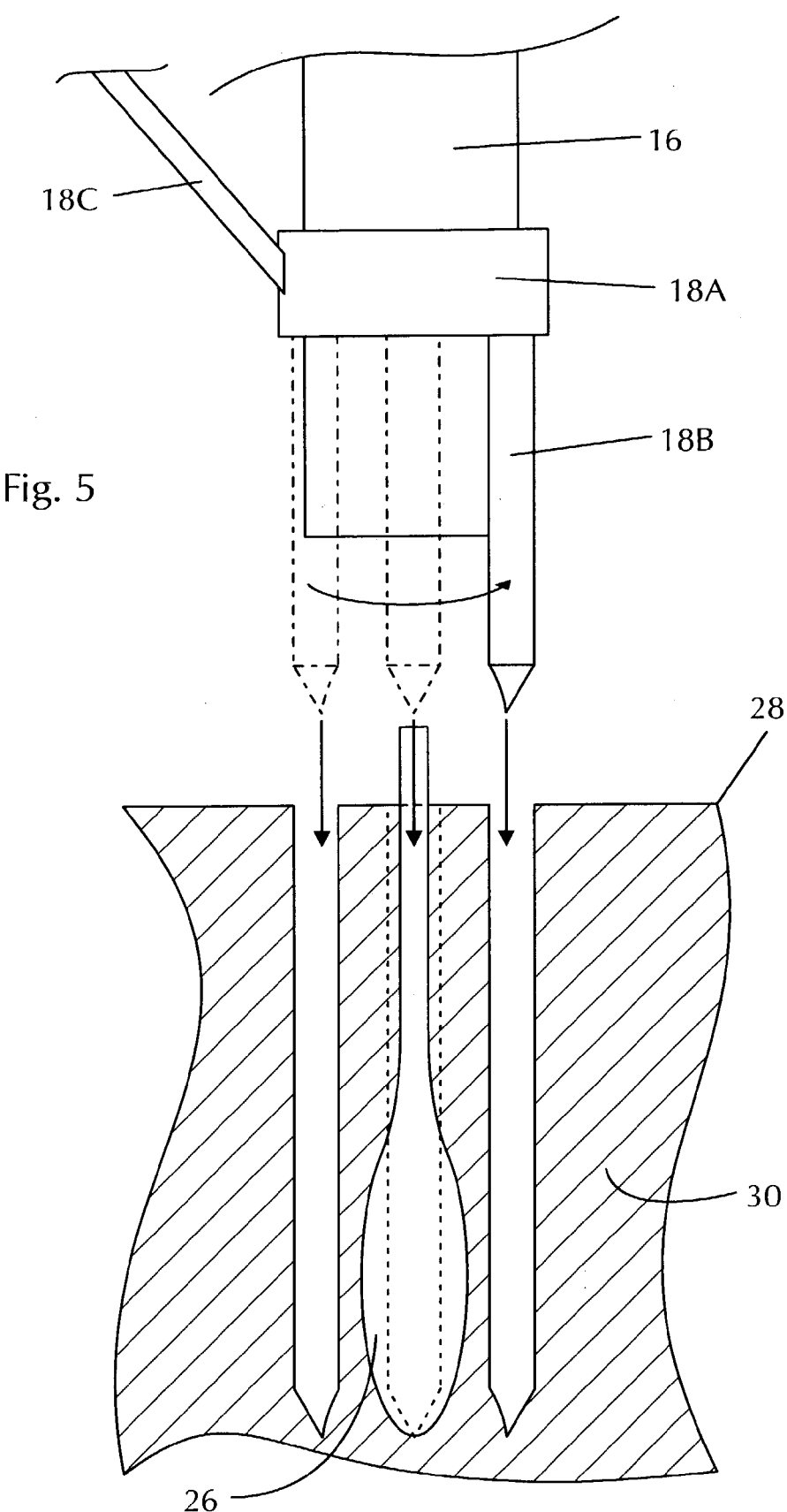
FIG. 5 is a side view of the present invention, illustrating the perforator in extended position above a follicular unit, and showing an outline of multiple incisions created by the punch with perforator. Specifically shown is the rotational pattern by which the single spike is repeatedly inserted around the follicular unit in question.

(14) and lower portion of the handle itself (12). The end of the extended member (18C) extends outwardly from the handle to allow the user to engage and same and slide the perforator down the punch, around which it is wrapped, to enter the scalp of the patient. Specifically shown in FIG. 5 is the rotational pattern by which the single spike is repeatedly inserted around the follicular unit in question. This provides a series of small apertures or "perforation" thereon.

The butt end of the handle (12) is inserted within a component of the suction means (20), such as via a tube fitting that wraps around the handle. It is to be understood that any appropriate suction means components, such as tubes, vacuum devices, and foot pedals that are known in the art may be utilized in conjunction with the method and apparatus of the present invention. The departure of the present invention from the prior art lies in the effective usage of the perforator device (18), as well as through the usage of suction for extraction and not collection purposes.

Figure 4:
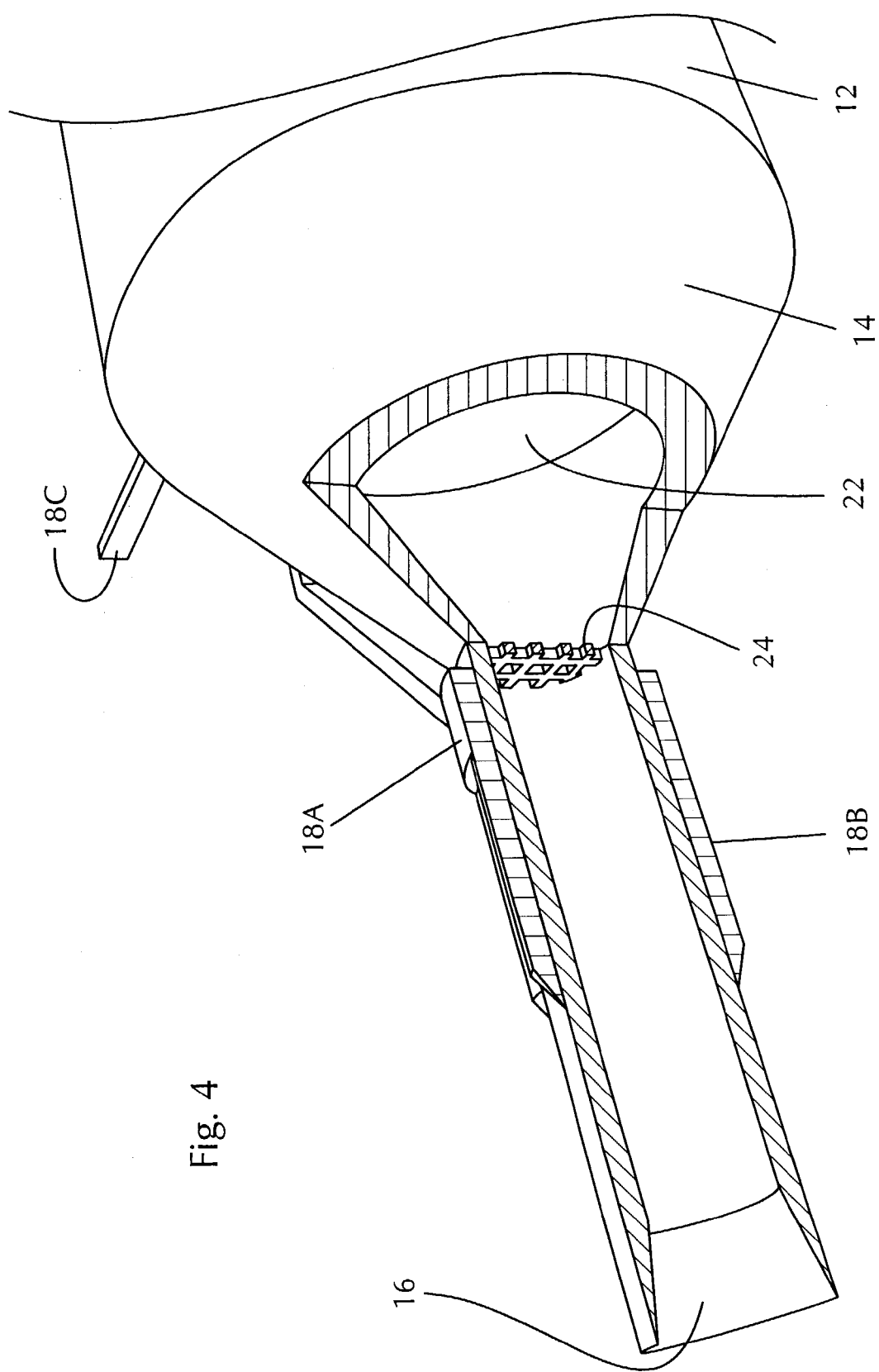
FIG. 4 is a three-quarter cut-away view of the present invention, illustrating the punch device, perforator, and follicular unit guard mechanism.

To illustrate the above in greater detail, FIG. 4 is a three-quarter cut-away view of the front end of the present invention, showing the punch (16), perforator (18), and guard mechanisms (24). Of particular importance is the guard member (24), which functions to contain successfully extracted follicular units. As noted, because the present method utilizes suction to facilitate extraction, rather than as a means of collection, the guard member (24) is needed to prevent the follicular units from entering aperture (22) into the suction device.

Lastly, FIG. 5 is a side view of the present invention, illustrating the perforator (18) in extended position above a follicular unit (26). The FIGURE also shows an outline of an incision created below the skin line (28) by the punch (16) with perforator (18), to a depth within the scalp area (30) that is similar to that of the follicular unit (26).

As shown, the spike (18B) of the perforator (18) is gently pushed below the skin line (30), creating a small apertures. Next, the user repeats the procedure at another location, such as a "three o'clock" or "six o'clock" position, relative to the center of the follicular unit in question. Importantly, because the spike (18B) is relatively thin, the incidence of piercing or damaging the follicular unit (26) is greatly mitigated. Moreover, the spike (18B) may be of a variety of diameter sizes consistent with these objectives.

Because the perforator weakens the structural integrity of the connective tissue, the follicular unit may be extracted considerably easier than through the usage of previous methods. As such, when suction is applied to the area in question, the follicular unit gives way, and is stopped by the guard member. Importantly, this method of extraction keeps the follicular unit intact for subsequent transplantation. Furthermore, the unique method of the present invention allows patients with naturally strong dermal tissue to become candidates for the transplantation procedure, as the usage of perforation and suction greatly facilitate extraction and mitigate the incidence of damaged follicular units.

Recent experimentation with the aforementioned method has yielded positive results, and it is believed that the method of the present invention may be conveniently adopted by all relevant medical professionals. Because the components of the apparatus of the present invention are relatively inexpensive to manufacture, it is believed that usage of the apparatus may be widespread in a relatively short period of time. Finally, because one utilizing this method need not constantly place the punch down and pick up forceps, the present method is considerably faster than the methods of the prior art, much to the benefit of both medical professionals and patients.

With regards to all descriptions and graphics, while the invention has been illustrated and described as embodied, it is not intended to be limited to the details shown, since it will be understood that various omissions, modifications, substitutions and changes in the forms and details of the device illustrated and in its operation can be made by those skilled in the art without departing in any way from the spirit of the invention.

Without further analysis, the foregoing will so fully reveal the gist of the present invention that others can readily adapt it for various applications without omitting features that, from the standpoint of prior art, constitute essential characteristics of the generic or specific aspects of this invention. What is claimed as new and desired to be protected by Letters Patent is set forth in the appended claims.

What is claimed is:

1. An apparatus for extraction of follicular units comprising:
    a generally elongated handle (12), which comprises a tapering portion (14) at an end thereof,
    a generally cylindrical biopsy punch (16) removably attached to the tapering portion of the handle (14),
    a perforator (18) affixed to the punch (16), comprising an annular portion (18A), which comprises an open end to allow the same to fit around the punch (16).
    the perforator further comprising a single solid spike member (18B), which extends along the vertical axis of the punch, generally parallel thereto,
    the perforator also comprising an extended member (18C), which is of a shape corresponding to the tapering portion of the handle (14) and lower portion of the handle (12) and abutting same,
    the end of the extended member (18C) extending outwardly from the handle to allow a user to engage and same and slide the perforator down the punch, to engage a patient's scalp, providing a small aperture, the repeating of same in different positions resulting in a perforation thereon,
    a butt end of the handle (12) engage a component of a suction means (20), which functions to vacuum extracted follicular units towards guard member (24), which contains follicular units and prevents same from entering an aperture (22) into the handle.

2. The apparatus as described in claim 1, wherein the punch is a 1 mm dermal biopsy punch.

3. The apparatus as described in claim 1, wherein the punch is inserted to approximately one half the depth of the follicular unit.

4. The apparatus as described in claim 1, wherein the handle is constructed of a polymeric material.

5. The apparatus as described in claim 1, wherein the punch is constructed of a metallic material.

6. A method of extracting follicular units comprising the steps of:
    utilizing an apparatus with a generally elongated handle (12), which comprises a tapering portion (14) at an end thereof,
    partially inserting a generally cylindrical biopsy punch (16), which is removably attached to the tapering portion of the handle (14), around a target follicular unit,
    inserting a perforator (18) around the target follicular unit, the perforator affixed to the punch (16), comprising an annular portion (18A), which comprises an open end to allow the same to fit around the punch (16), the perforator further comprising single solid spike member (18B), which extends along the vertical axis of the punch, generally parallel thereto, the perforator also comprising an extended member (18C), which is of a shape corresponding the tapering portion of the handle (14) and lower portion of the handle (12) and abutting same, the end of the extended member (18C) extending outwardly from the handle to allow a user to engage and same and slide the perforator down the punch, to engage a patient's scalp, providing an aperture, the repeating of the same in different positions resulting in a perforation thereon, utilizing a suction means affixed to a butt end of the handle (12), which functions to vacuum extracted follicular units towards a guard member (24), which contains follicular units and prevents same from entering an aperture (22) into the handle.

7. The method as described in claim 6, utilizing a 1 mm dermal biopsy punch.

8. The method as described in claim 6, wherein the punch is inserted to approximately one half the depth of the follicular unit.

9. The method as described in claim 6, utilizing a handle constructed of a polymeric material.

10. The method as described in claim 6, utilizing a punch constructed of a metallic material.

11. The method according to claim 6, wherein the apparatus for extraction of follicular units includes:

the generally elongated handle (12), which includes the tapering portion (14) at an end thereof, the generally cylindrical biopsy punch (16) removably attached to the tapering portion of the handle (14), the perforator (18) affixed to the punch (16), including the annular portion (18A), which includes the open end to allow the same to fit around the punch (16), the perforator further including the single solid spike member (18B), which extends along the vertical axis of the punch, generally parallel thereto, the perforator also including the extended member (18C), which is of a shape corresponding to the tapering portion of the handle (14) and lower portion of the handle (12) and abutting same, the end of the extended member (18C) extending outwardly from the handle to allow a user to engage and same and slide the perforator down the punch, to engage a patient's scalp, providing a small aperture, the repeating of same in different positions resulting in a perforation thereon, the butt end of the handle (12) engage the component of the suction means (20), which functions to vacuum extracted follicular units towards the guard member (24), which contains follicular units and prevents same from entering the aperture (22) into the handle.

* * * * *